United States Patent
Tripathy et al.

(10) Patent No.: US 7,294,686 B2
(45) Date of Patent: Nov. 13, 2007

(54) POLYMERIZATION OF AROMATIC MONOMERS USING DERIVATIVES OF HEMATIN

(75) Inventors: Sukant Tripathy, deceased, late of Acton, MA (US); by Susan Tripathy, legal representative, Acton, MA (US); Lynne A. Samuelson, Marlborough, MA (US); Ferdinando F. Bruno, Andover, MA (US); Sucharita Roy, Tewksbury, MA (US); Ramaswamy Nagarajan, Dracut, MA (US); Jayant Kumar, Westford, MA (US); Bon-Cheol Ku, Cambridge, MA (US); Soo-Hyoung Lee, Lowell, MA (US)

(73) Assignees: University of Massachusetts Lowell, Lowell, MA (US); United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/337,964

(22) Filed: Jan. 23, 2006

(65) Prior Publication Data

US 2007/0021587 A1    Jan. 25, 2007

Related U.S. Application Data

(60) Continuation of application No. 10/826,623, filed on Apr. 16, 2004, now abandoned, which is a division of application No. 09/994,998, filed on Nov. 27, 2001, now abandoned.

(60) Provisional application No. 60/253,109, filed on Nov. 27, 2000.

(51) Int. Cl.
  *C08G 73/06* (2006.01)
  *C08F 2/04* (2006.01)
  *C08F 4/26* (2006.01)

(52) U.S. Cl. ............ 528/424; 528/423; 528/422; 528/486; 528/491; 526/217; 536/23.1; 540/645; 502/325; 502/338

(58) Field of Classification Search ............ 528/424, 528/423, 422, 486, 491; 526/217; 536/23.1; 540/645; 502/325, 338
See application file for complete search history.

(56) References Cited

U.S. PATENT DOCUMENTS 5,143,828 A    9/1992    Akkara et al.
5,253,100 A    10/1993    Yang et al.

(Continued)

OTHER PUBLICATIONS

Akkara, J.A., et al., "Hematin catalyzed polymerization of phenol compounds", Macromolecules 33: 2377-2382 (2000).*

(Continued)

*Primary Examiner*—Duc Truong
(74) *Attorney, Agent, or Firm*—Hamilton, Brook, Smith & Reynolds, P.C.

(57) ABSTRACT

Hematin, a hydroxyferriprotoporphyrin, is derivatized with one or more non-proteinaceous amphipathic groups. The derivatized hematin can serve as a mimic of horseradish peroxidase in polymerizing aromatic monomers, such as aromatic compounds. These derivatized hematins can also be used as catalysts in polymerizing aromatic monomers, and can exhibit significantly greater catalytic activity than underivatized hematin in acidic solutions. In one embodiment, polymerization is in the presence of a template, along which aromatic monomers align. An assembled hematin includes alternating layers of hematin and a polyelectrolyte, which are deposited on an electrically charged substrate. Assembled hematin can also be used to polymerize aromatic monomers.

23 Claims, 15 Drawing Sheets

U.S. PATENT DOCUMENTS

| | | | |
|---|---|---|---|
| 5,370,825 A | 12/1994 | Angelopoulos et al. | |
| 5,420,237 A | 5/1995 | Zemel et al. | |
| 5,489,400 A | 2/1996 | Liu et al. | |
| 5,711,867 A * | 1/1998 | Przybycien et al. | 205/688 |
| 5,994,498 A | 11/1999 | Tripathy et al. | |
| 6,018,018 A | 1/2000 | Samuelson et al. | |
| 6,150,491 A | 11/2000 | Akkara | |

OTHER PUBLICATIONS

Tzou, K., and Gregory, R.V., "A Method to Prepare Soluable Polyaniline Salt Solutions—in situ Doping of PANI base with Organic Dopants in Polar Solvents,"*Synthetic Metals*, 53: 365-377 (1993).

Nguyen, M.T., et al., "Synthesis and Properties of Novel Water-Soluble Conducting Polyaniline Copolymers," *Macromolecules*,27: 3625-3631 (1994).

Shannon, K. and Fernandez, J.E., "Preparation and Properties of Water-Soluble, Poly(Styrenesulfonic Acid)-Doped Polyaniline," *J. Chem. Soc., Chem. Comm.*, 643-644 (1994).

Tanaka, K., et al., "Doping Effect of $C_{60}$ on Soluble Polyaniline," *Synthetic Metals*, 66: 193-196 (1994).

Ferreira, M., et al., "Molecular Self-Assembly of Conjugated Polyions: A New Process for Fabricating Multilayer Film Heterostructures," *Thin Solid Films*, 244: 806-809 (1994).

Ng, S.C., et al., "Poly(*o*-Aminobenzylphosphonic Acid): A Novel Water Soluble, Self-Doped Functionalized Polyaniline," *J. Chem. Soc., Chem. Commun.*, 1327-1328 (1995).

Chen, S., and Hwang G., "Synthesis of Water-Soluble Self-Acid-Doped Polyaniline," *J. Am. Chem. Soc.*, 116: 7939-7940 (1994).

Chen, S. and Hwang, G., "Water-Soluble Self-Acid-Doped Conducting Polyaniline: Structure and Properties," *J. Am. Chem. Soc.*, 117: 10055-10062 (1995).

Chan, H.S.O., et al., "A New Water-Soluble, Self-Doping Conducting Polyaniline From Poly(*o*-aminobenzylphosphonic acid) and its Sodium Salts: Synthesis and Characterization," *J. Am. Chem. Soc.*, 117: 8517-8523 (1995).

Dordick, J.S., et al., "Peroxidases Depolymerize Lignin in Organic Media But Not in Water," *Proc. Natl. Acad. Sci. USA*, 83: 6255-6257 (1986).

Dordick J.S., et al., "Polymerization of Phenols Catalyzed by Peroxidase in Nonaqueous Media," *Biotechnology and Bioengineering*, 30: 31-36 (1987).

Kazandjian, R. Z., et al., "Enzymatic Analyses in Organic Solvents," *Biotechnology and Bioengineering*, 28:417-421 (1986).

Klibanov, A.M., et al., "Enzymatic Removal of Toxic Phenols and Anilines from Waste Waters," *J. Appl. Biochem.*, 2: 414-421 (1980).

Sakaki, J., et al., "Lipase-Catalyzed Asymmetric Synthesis of 6-(3-chloro-2-hydroxpropyl)-1,3-dioxin-4-ones and their Conversion to Chiral 5,6-Epoxyhexanoates," *Tetrahedron: Asymmetry*, 2:343-346 (1991).

Ikeda, R., et al., "Novel Synthetic Pathway to a poly (phenylene oxide). Laccase-Catalyzed Oxidative Polymerization of Syringic Acid," *Macromolecules*, 29: 3053-3054 (1996).

Akkara, J.A., et al.,. "Synthesis and Characterization of Polymers Produced by Horseradish Peroxidase in Dioxane," *J. Polymer Sci.: Part A: Polymer Chemistry*, 29: 1561-1574 (1991).

Klibanov, A.M. and Morris, E.D., "Horseradish Peroxidase for the Removal of Carcinogenic Aromatic Amines from Water," *Enzyme Microb. Technol.*, 3: 119-122 (1981).

Ayyagari, M.S., et al., "Controlled Free-Radical Polymerization of Phenol Derivatives by Enzyme-Catalyzed Reactions in Organic Solvents," *Macromolecules*28: 5192-5197 (1995).

Bruno, F.F., et al., "Enzymatic Mediated Synthesis of Conjugated Polymers at the Langmuir Through Air-Water Interface,"*Langmuir*, 11: 889-892 (1995).

Lapkowski, M., "Electrochemical Synthesis of Linear Polyaniline in Aqueous Solutions," *Synthetic Metals*, 35:169-182 (1990).

March, J., in *Advanced Organic Chemistry—Reactions, Mechanisms, and Structure* (NY: Magraw-Hill Company), pp. 667, 668 (1977).

Shinohara, H., et al., "Enzyme Microsensor for Glucose with an Electro-Chemically Synthesized Enzyme-Polyaniline Film," *Sensors and Actuators*, 13: 79-86 (1988).

Alva, K.S., et al., "Biochemical Synthesis of Water Soluble Polyanilines: poly(p-aminobenzoic acid)," *Macromol. Rapid Comm.*, 17: 859-863 (1996).

Liao, Y., and Levon, K., "Solubilization of Polyaniline in Water by Interpolymer Complexation," *Macromol. Rapid Commun.*, 16: 393-397 (1995).

Excerpts from "Plastics Engineering: Plastics—Saving Planet Earth," vol. LIII, No. 3 (Toronto; Mar. 1997).

Westerweele, E., et al., "Inverted'Polmer Light-Emitting Diodes on Cylindrical Metal Substrates," *Advanced Materials*, 7(9): 788-790 (1995).

Ryu, K., et al., "Peroxidase-Catalyzed Polymerization of Phenols: Kinetics of p-Cresol Oxidation in Orgainc Media," *American Chemical Society Symp. Ser.*, 389: 141-157 (1989).

Alva, K.S., et al., "Novel Immobilization Techniques in the Fabrication of Efficient Eletrochemical Biosensors,"*SPIE*, 2716: 152-163(1996).

Genies, E.M., et al., "A Rechargeable Battery of the Type Polyaniline/Propylene Carbonate—LiC1O4/Li-Al," *Journal of Applied Electrochemistry 18*: 751-756 (1988).

Samuelson, L.A., et al., "Biologically Derived Conducting and Water Soluble Polyaniline," *Macromolecules 31*: 4376-4378 (1998).

Liu, W., et al., "Enzymatically Synthesized Conducting Polyaniline," *J. Am. Chem. Soc.* 121: 71-78 (1999).

Zhang, Q.M., et al., "Enzymatic Template Synthesis of Polyphenol," *Materials Research Society 600*: 255-259 (2000).

Akkara, J.A., et al., "Hematin-Catalyzed Polymerization of Phenol Compounds," *Macromolecules 33*: 2377-2382 (2000).

Dordick, J. S., "Enzymatic Catalysis in Monophasic Organic Solvents," *Eynzyme Microbial Technology 11*: 194-211 (1989).

Dunford, H.B., "Horseradish Peroxidase: Structure and Kinetic Properties," In *Peroxidase in Chemistry and Biology* vol. II, J. Everse, et al., eds (FL: CRC Press, Inc.), pp. 2-17 (1991).

Wudl, F., et al., "Poly(p-phenyleneamineimine): Synthesis and Comparison to Polyaniline" *J. Am. Chem. Soc. 109*: 3677-3684 (1987).

Stafström, S., et al., "Polaron Lattice in Highly Conducting Polyaniline: Theoretical and Optical Studies," *The American Physical Society 59*: 1464-1467 (1987).

Shacklette, L. W., et al., "EMI Shielding of Intrinsically Conductive Polymers,"*In Search of Excellence by Society of Plastic Engineers and Plastics Engineering* 665-667 (1991).

Przybycien, P.R., et al., "Electrochemical Separation Utilizing Metalloporphyrins and Metallophthalocyanines," *Chem. Abstract*, 128: 162418 (1998).

\* cited by examiner

POLYMERIZATION OF AROMATIC MONOMERS USING DERIVATIVES OF HEMATIN

RELATED APPLICATIONS

This application is a continuation of U.S. application Ser. No. 10/826,623, filed on Apr. 16, 2004 abandoned, which is a divisional of U.S. application Ser. No. 09/994,998, filed Nov. 27, 2001 abandoned, which claims the benefit of U.S. Provisional Application No. 60/253,109, filed on Nov. 27, 2000. The entire teachings of the above applications are incorporated herein by reference.

GOVERNMENT SUPPORT

The invention was supported, in whole or in part, by a grant ONR N0014-00-1-0718 from the Office of Naval Research and a grant DAAD 16-01-C-0011 from the U.S. Army Research Office. The Government has certain rights in the invention.

BACKGROUND OF THE INVENTION

Recently, there has been an increased interest in tailored development of polyaromatic polymers, particularly polyaromatic polymers that are electrically conductive and/or have interesting and useful optical properties. Examples of electrically conductive polymers include certain polyanilines, polythiophenes, polypyrroles, and polyphenols. These conductive polyaromatic polymers may be used in a variety of electronic devices, including electro-chromic devices, light-emitting diodes, electrostatic discharge protection, and light weight batteries. Of these polyaromatic polymers, polyanilines are the most extensively studied, due largely to superior electrical properties such as high discharge capacity.

In addition to the above-named electrical properties, the thermal and structural properties of polyphenols have long been exploited. In particular, phenol-formaldehyde resins such as novolacs and resols have found wide application as wood composites, laminates, foundry resins, abrasives, friction and molding materials, coatings and adhesives, fiber binders, and flame retardants. The use of formaldehyde in polyphenol synthesis, however, presents a significant toxicological and environmental hazard.

Despite the industrial utility of polyaromatic polymers, their synthesis remains problematic. Known difficulties in the synthesis of these polymers include inconsistent product composition, due in part to extensive branching of the polymers. In addition, many of the polyaromatic polymers are insoluble or sparingly soluble in common solvents, leading to poor processability. The use of toxic reagents, as noted above, is another undesirable feature of current synthetic methods. A search for new methods of synthesizing polyaromatic polymers has not yet yielded a commercially viable approach.

Many of the synthetic approaches to forming polyaromatic polymers use a heme-containing enzyme to catalyze the polymerization. Any such catalyst must necessarily be stable and active under acidic conditions, as acidic conditions are required in order to synthesize an electrically conductive form of a polyaromatic polymer such as polyaniline. An example of an enzyme extensively studied for aromatic molecule polymerization is horseradish peroxidase. Unfortunately, horseradish peroxidase and other peroxidases are inactive at low pH and are prohibitively expensive to use commercially. Hematin has been used to mimic the catalytic activity of horseradish peroxidase. However, despite its lower cost, hematin is a non-ideal catalyst for commercial polymerizations because of its low solubility in acidic, aqueous media. The low solubility of hematin under these conditions leads to a low rate of polymerization and poor yields. Therefore, a need exists to develop a low cost, high efficiency means of synthesizing polyaromatic polymers, which is compatible with conditions required to synthesize polymers with commercially desirable properties.

SUMMARY OF THE INVENTION

The invention generally is directed to a derivatized hematin; a method for polymerizing an aromatic monomer with an assembled hematin or a derivatized hematin; and to methods of forming the assembled and derivatized hematins.

In one embodiment, the invention includes hematin derivatized with one or more non-proteinaceous amphipathic groups. In a preferred embodiment, the amphipathic group is polyethylene glycol.

In another embodiment, the invention includes a method of polymerizing aromatic monomers such as anilines or phenols. In a preferred embodiment, the polymerization takes place in the presence of a template. Typically, the template is anionic.

In another embodiment, the invention includes a method for preparing a derivatized hematin, by reacting hematin with an amphipathic compound. In a preferred embodiment, the hematin is derivatized with an amphipathic compound in the presence of a carboxylic acid activating compound and an aprotic base.

In yet another embodiment, the invention includes an assembled hematin, which includes alternating layers of hematin and a polyelectrolyte on an electrically charged substrate. Preferably, the polyelectrolyte is cationic.

In another embodiment, the invention includes a method of polymerizing aromatic monomers by contacting an aromatic monomer and a template with the assembled hematin. In a preferred embodiment, the aromatic monomer is an aniline or a phenol.

In another embodiment, the invention includes a method of forming assembled hematin, by alternately depositing one or more layers of hematin and one or more layers of a polyelectrolyte on an electrically charged substrate.

Advantages of the present invention include resolving the current limitations of catalysts used in the commercial synthesis of polyaromatic polymers, by reducing the cost of the catalyst and by providing a catalyst that is active and stable over a wide range of pHs. The derivatized hematins of the present invention are also water-soluble and recyclable, virtually eliminating the need for toxic reagents and solvents, and thus creating an environmentally friendly synthesis for polyaromatic polymers. In addition, the derivatized hematins of the present invention, in a combination with a template, reduce the amount of branching during polymerization, leading to a structurally more consistent product.

DETAILED DESCRIPTION OF THE INVENTION

Figure 1:
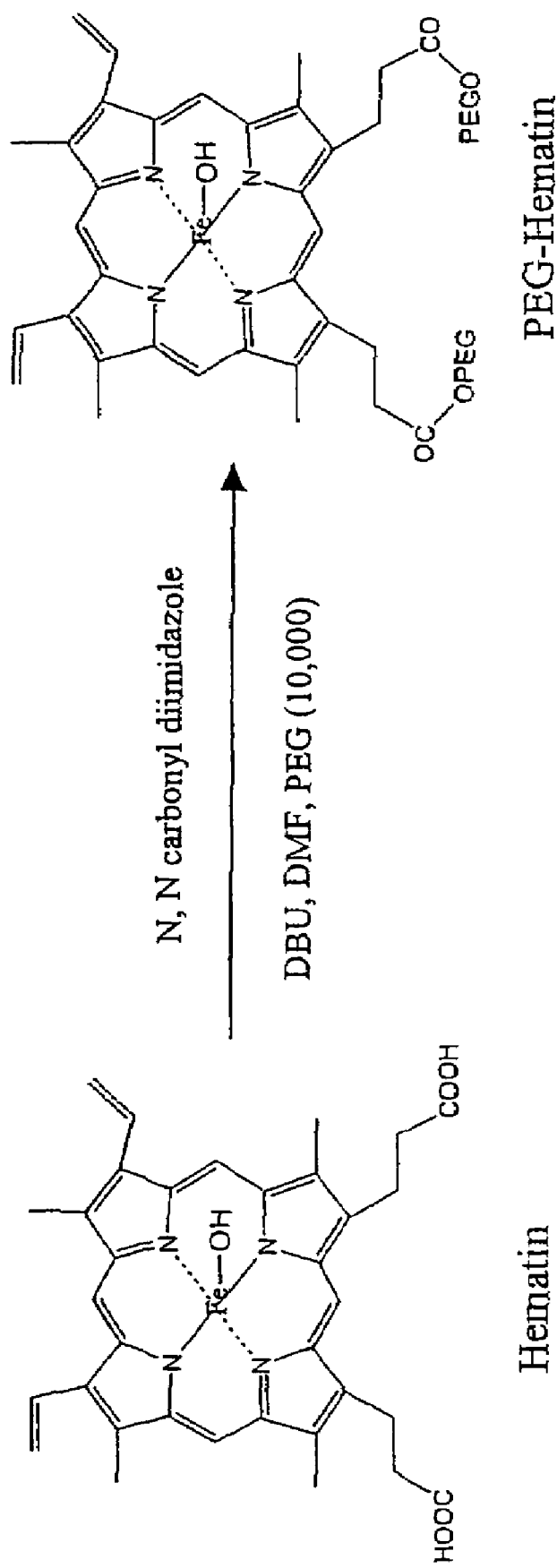
FIG. 1 shows the functionalization of hematin with polyethylene glycol (PEG) in the presence of N,N'-carbonyl diimidazole, 1,8-diazabicyclo[5.4.0]undec-7-ene (DBU) and dimethylformamide (DMF).

The present invention generally includes a derivatized hematin and an assembled hematin, along with methods of preparing the hematins. The invention also includes methods of polymerizing aromatic monomers in a reaction catalyzed by an assembled hematin or a derivatized hematin.

The present invention includes hematin, a hydroxyferriprotoporphyrin, which has been derivatized with one or more non-proteinaceous amphipathic groups. Examples of amphipathic groups include phosphoglycerides; sphingomyelin; glycolipids; substituted or unsubstituted polyethers and polyalkylene glycols; substituted or unsubstituted polyamines such as polyethyleneimine, polyallylamine, and poly(diallylamine); polyammonium groups, such as poly (allylammonium salts), poly(trimethylallylammonium salts), poly(triethylallylammonium salts), poly(dimethyldiallylammonium salts), poly(diethyldiallylammonium salts); and polysaccharides such as hydroxypropyl cellulose, hydroxymethyl cellulose, and hydroxyethyl cellulose.

Preferred amphipathic groups include polyalkylene glycols such as polyethylene glycol and polypropylene glycol. Preferably, polyethylene glycol groups have a molecular weight of about 400 to about 100,000, or more preferably, a molecular weight of about 5,000 to about 15,000.

In another embodiment, the hematin derivatized with an amphipathic group is soluble over a pH range from about pH 1 to about pH 12.

In another embodiment, the present invention includes a method of polymerizing an aromatic monomer, which includes combining the aromatic monomer with a derivatized hematin catalyst. In a preferred embodiment, the hematin is derivatized with polyethylene glycol. In another preferred embodiment, the derivatized hematin catalyst and the aromatic monomer are additionally combined with a peroxide to initiate the reaction.

Aromatic monomers include substituted or unsubstituted aromatic compounds. Suitable aromatic compounds include 4-(p-hydroxyphenylazo)pyridine and 4-(p-hydroxyphenylazo)pyridinium methiodide. Preferred aromatic compounds for polymerization include aniline, phenol, and 2-methoxy-5-methylaniline.

Suitable substituents on aromatic monomers will not significantly reduce the rate of polymerization as compared to an unsubstituted aromatic monomer (e.g., will not reduce the rate of polymerization by more than ten-fold). Examples of suitable substituents for aromatic monomers include, for example, halogen (—Br, —Cl, —I, and —F), —OR, —CN, —$NO_2$, —COOR, —CONR$R_1$, —$SO_kR$ (where k is 0, 1, or 2), —NR$R_1$, —SR, haloalkyl groups, and —NH—C(=NH)—$NH_2$. R and $R_1$ are independently, —H, an aliphatic group, an aralkyl group, a heteroaralkyl group, an aromatic group, or a substituted aromatic group. A substituted aromatic monomer can have more than one substituent.

In a preferred embodiment of the present invention, a template is combined with the derivatized hematin, an aromatic monomer, and a peroxide, such that the aromatic monomer aligns along the template and polymerizes to form a complex including the polymerized aromatic monomer and the template. A "template," as that term is employed herein, is defined as a polymer or oligomer that can bind, such as ionically bind, to the aromatic monomer being polymerized according to the method of the invention.

Suitable template polymers include polyelectrolytes such as an anionic polymer or a cationic polymer. Anionic polymer templates include polymers that include pendant acid functional groups such as poly(vinylbenzoic acid) and salts thereof, poly(vinyl polyphosphonic acid) and salts thereof, poly(glutamic acid) and salts thereof, poly(aspartic acid) and salts thereof, poly(acrylic acid), and poly(maleic acid co-olefin) and salts thereof. Co-olefins that can be polymerized with maleic acid to form poly(maleic acid co-olefin) include 1-propene, 1-butene, 1-pentene, 1-hexene, 1-heptene, 1-octene, 1-nonene, and 1-decene. Preferred anionic polymer templates include poly(styrene sulfonic acid) and salts thereof, lignin sulfonic acid and salts thereof, and dodecylbenzene sulfonic acid and salts thereof.

Optically active templates can also be employed in the polymerization method of the invention. When an optically active template is employed, the template can induce macroasymmetry in the polymerized aromatic monomer due to the close association of the template with the polymerized aromatic monomer in the complex. Examples of optically active templates include polynucleic acids and salts thereof, such as ribonucleic acids and 2'-deoxyribonucleic acids. Other suitable templates include biological receptors, peptides, proteins, zeolites, caged compounds, phenol red, azo compounds, azo polymers, and dendrimers.

In a preferred embodiment, the complex of a polymerized aromatic monomer and a template is a water-soluble complex of a polyaniline and a template. Even more preferably, the polyaniline is of the electrically-conducting emeraldine salt form. Emeraldine is an electrically-conducting form of polyaniline, and has a characteristic green color when protonated, or doped.

In another preferred embodiment, the complex including a polymerized aromatic monomer and a template is a water-soluble complex of a polyphenol and a template.

In yet another preferred embodiment, a polymerized aromatic monomer complexed to an optically active template has a macro-asymmetry.

A complex of a polymerized aromatic monomer and a template can be prepared by contacting an aromatic monomer, such as an aniline or a phenol, and a template with a derivatized hematin in a solution having a pH from about 0 to about 12. Preferably, the solution is buffered, and the pH ranges from about 0 to about 7, and more preferably ranges from about pH 0 to about pH 4. The ratio of aromatic monomer to template (measured as the concentration of template repeat units) can vary from 5:1 to 1:5 (aromatic monomer:template repeat unit), and is preferably from about 2:1 to about 1:2, and is even more preferably about 1:1. A catalytic amount of the derivatized hematin can be added to the reaction mixture either before or after addition of the aromatic monomer. A catalytic amount of the derivatized hematin is typically between about one unit/mL and five units/mL, where one unit will form 1.0 mg purpurogallin from pyrogallol in 20 seconds at pH 6.0 at 20° C. Preferably, the derivatized hematin is added to the solution after addition of the template and aromatic monomer. In a preferred embodiment, a peroxide is also added to the reaction mixture. The peroxide is added incrementally, such as not to de-activate the derivatized hematin catalyst, until an amount approximately stoichiometric with the amount of aromatic monomer has been added. The reaction can be monitored spectroscopically.

The above polymerization can be carried out in polar solvents such as ethanol, methanol, isopropanol, dimethylformamide, dioxane, acetonitrile, and diethyl ether, but is preferably carried out in water.

In one embodiment, the present invention is a method of derivatizing hematin, which includes reacting hematin with one or more amphipathic compounds, thereby forming a derivatized hematin. In a preferred embodiment, the hematin is reacted with one or more amphipathic compounds in the presence of a carboxylic acid activating compound and an aprotic base. In a more preferable embodiment, the carboxylic acid activating compound is a dialkylcarbodiimide. In another preferred embodiment, the amphipathic compound is a substituted or unsubstituted polyalkylene glycol. Even more preferably, the polyalkylene glycol is polyethylene glycol.

"Carboxylic acid activating compounds," as used in the present invention, are compounds that serve to couple a nucleophile, such as a hydroxyl, amine, or thiol group, to a carboxylic acid, thereby forming an ester, an amide, or a thioester linkage. Suitable carboxylic acid activating compounds include dialkylcarbodiimides, preferably diisopropylcarbodiimide and dicyclohexylcarbodiimide; N,N'-carbonyldiimidazole; nitrophenol, preferably o-nitrophenol and p-nitrophenol; pentahalophenol, preferably pentachlorophenol, and pentabromophenol; N-hydroxysuccinimide; tosyl chloride; 1-hydroxybenzotriazole; and N-ethyl-N'-(3-dimethylaminopropyl)carbodiimide.

"Aprotic bases," as used in the present invention, include bases without an exchangeable proton. Suitable aprotic bases include trialkylamines, such as trimethylamine, triethylamine, diisopropylethylamine and triphenylamine; pyridine; pyrimidine; 1,8-diazabicyclo[5.4.0]undec-7-ene (DBU); and 1,3,5-triazine.

Derivatized hematins of the present invention can be prepared, for example, by reacting about one-half to about ten mole equivalents of an amphipathic compound, such as polyethylene glycol, with hematin in the presence of an excess of a carboxylic acid activating compound, and an aprotic base, in an aprotic solvent such as dimethylformamide or an ether. The mixture is allowed to stir for about 6 hours to about 6 days, and is then quenched with a large volume of water or other protic solvent. The unreacted reagents are removed by extraction of the reaction mixture with an organic solvent such as ethyl acetate. The water layer is concentrated, preferably by lyophilization, to yield the derivatized hematin.

In another embodiment, the present invention is assembled hematin, which includes one or more layers of hematin alternating with one or more layers of a polyelectrolyte deposited on a substrate. In a preferred embodiment, the polyelectrolyte is a cationic polymer, such as a poly(dialkyldiallylammonium salt) or a poly(trialkylallylammonium salt). More preferably, the polyelectrolyte is poly(dimethyldiallylammonium chloride).

In another embodiment, the present invention includes a method of a polymerizing an aromatic monomer to form a complex of a polymerized aromatic monomer and a template, by contacting the aromatic monomer and the template with the assembled hematin. Preferably, the template is an anionic polymer, such as poly(styrene sulfonic acid) or a salt thereof. In another preferred embodiment, the aromatic monomer is a substituted or unsubstituted aromatic compound, such as an aniline or a phenol. In yet another preferred embodiment, the complex of the polymerized aromatic monomer and the template forms in solution or the complex forms on the assembled hematin. The complex forming on the assembled hematin can contact one or more layers of hematin or the polyelectrolyte.

In another embodiment, the present invention includes a method of forming assembled hematin, by alternately depositing layers of hematin and a polyelectrolyte onto an electrically charged substrate. Preferably, the polyelectrolyte is a cationic polymer, and more preferably is a poly(dialkyldiallylammonium salt) or a (trialkylallylammonium salt), such as poly(dimethyldiallylammonium chloride).

Assembled hematins of the present invention can be prepared, for example, by dipping a charged substrate, such as a negatively-charged hydrophilized glass slide, into about 0.1 mM to about 100 mM hematin having a pH from about 6 to about 12 at about 0° C. to about 50° C. for about 1 minute to about 100 minutes. The substrate is washed with deionized water and dried with a stream of gas, such as nitrogen or argon. The substrate with a single layer of hematin is dipped into about 0.1 mM to about 100 mM polyelectrolyte having a pH from about 6 to about 12 at about 0° C. to about 50° C. for about 1 minute to about 100 minutes. The substrate is washed with deionized water and dried with a stream of gas, such as nitrogen or argon. The process can then be repeated, from about 1 to about 100 times, to produce multiple alternating layers (or bilayers) of hematin and the polyelectrolyte on the substrate. For a positively-charged substrate, the order of dipping into hematin and a polyelectrolyte is reversed.

Polymerizations catalyzed by assembled hematins of the present invention can be carried out, for example, in a buffered solution, ranging from about pH 1 to about pH 12, at about 0° C. to about 50° C. An aromatic monomer and a template are added to the buffered solution, such that the ratio of aromatic monomer to template repeat unit is about 5 to 1 to about 1 to 5. The concentration of aromatic monomer is about 0.01 M to about 1 M. A quantity of assembled hematin, including about 2 to about 100 bilayers of hematin and polyelectrolyte, is added to the solution. A solution of a peroxide, in an amount sufficient to polymerize the aromatic monomer, is added dropwise over about 5 minutes to about 200 minutes. The reaction is maintained for about 1 hour to about 200 hours. The progress of the reaction can be monitored spectrophotometrically.

A peroxide, as used in the present invention, is an organic or inorganic compound that includes a —O—O— bond, such as ROOR, where R is as defined above. Preferably, one R is hydrogen, to give ROOH. Even more preferably, the peroxide is hydrogen peroxide, HOOH.

Suitable substrates for assembled hematin are any solids that can maintain an electrical charge. Examples of substrates include glasses (e.g., pyrex and glass slides), plastics (e.g., poly(vinyl chloride) and poly(ethylene)), ceramics, metals, and the like. Preferred substrates are glass slides, which have been hydrophilized with an aqueous alkali solution, such as Chem-solv, under ultrasonication.

The present invention will now be further described by the following non-limiting examples.

EXAMPLE 1

Synthesis of PEG-Hematin Complex

The PEG-hematin complex was obtained through the coupling of polyethylene glycol (PEG) chains to a hematin molecule through ester linkages as shown in FIG. 1. The PEG-hematin complex was prepared by the addition of a mole equivalent of PEG (19 mg) to hematin (200 mg) in the presence of activators N,N'-carbonyldiimidazole (0.05 g) and 1,8-diazabicyclo[5.4.0]undec-7-ene (DBU) (0.047 g) in DMF. The mixture was allowed to stir for 48 hours then was quenched by the addition of a large volume of deionized water. The unreacted reagents were removed by extraction with ethyl acetate. The water layer was subsequently lyophilized to yield PEG-hematin as a reddish-brown solid.

The complex was characterized using NMR and FTIR spectroscopy. The average extent of modification of the acidic groups of hematin was determined using UV-vis spectroscopy. The UV-vis spectra of the PEG-hematin exhibited a decrease in the Soret band (420 nm), a porphyrin centered π-π* transition, in comparison to hematin, which was used to calculate the amount of hematin present in the sample. However, the energy and spectral bandwidths of PEG-hematin were indistinguishable from hematin, which indicated that the modification of hematin by poly (ethylene glycol) does not affect the heme structure. Based on this assumption, the average concentration of hematin in the PEG-hematin sample was subsequently determined to be 67% by weight.

Figure 2:
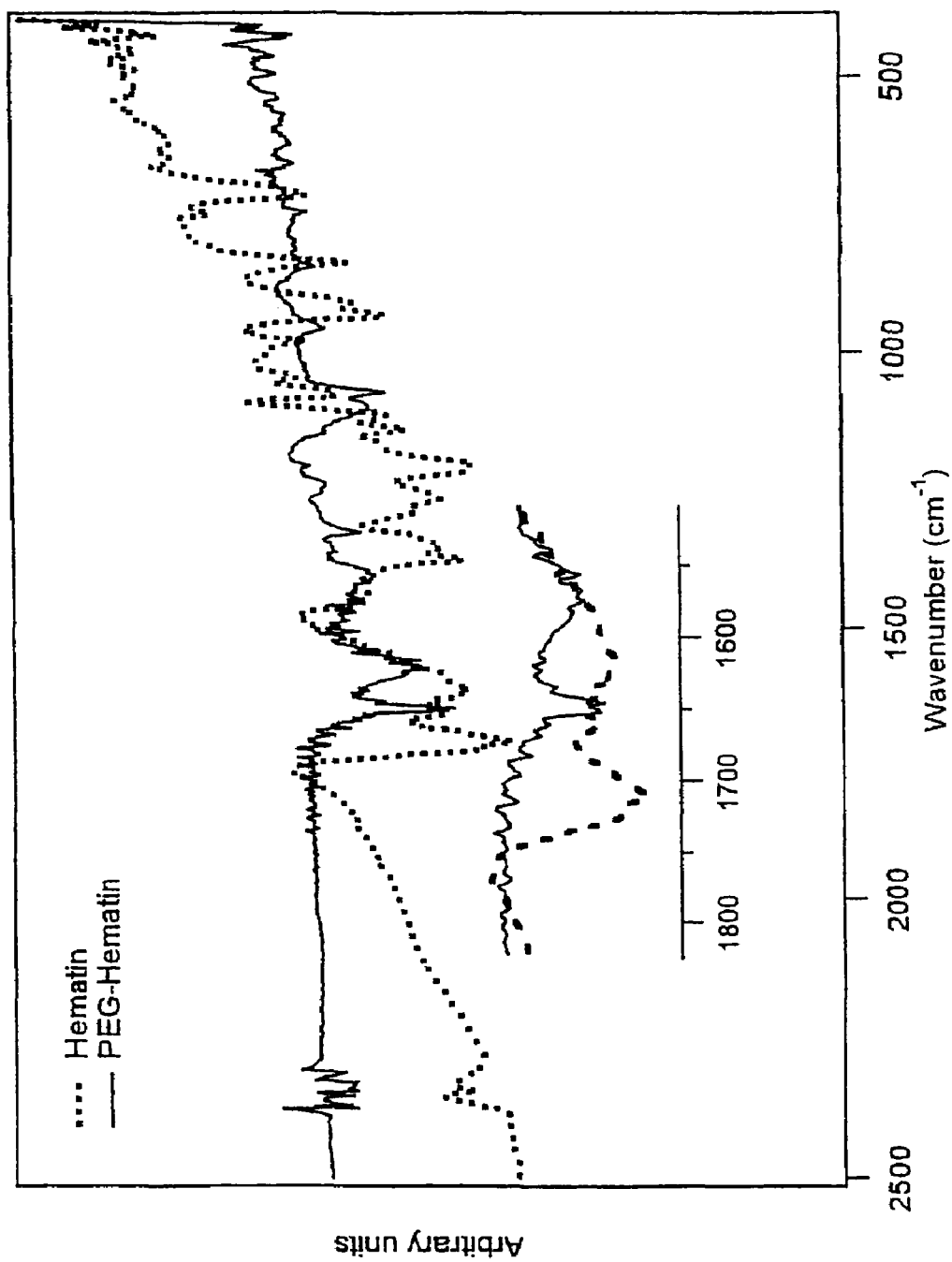
FIG. 2 shows the FTIR spectra of hematin and PEG-hematin. The inset shows an expanded region between 1500 and 1700 $cm^{-1}$.

An FTIR spectrum of PEG-hematin indicated the presence of an ester functionality by the appearance of a doublet at 1646 and 1651 cm$^{-1}$ (similar to diethyl phthalate) accompanied by the complete disappearance of the peak at 1712 cm$^{-1}$ for the acid carbonyl of hematin (FIG. 2). The strong peak at 1100 cm$^{-1}$ corresponded to the ether linkage of the glycol moiety.

Figure 3:
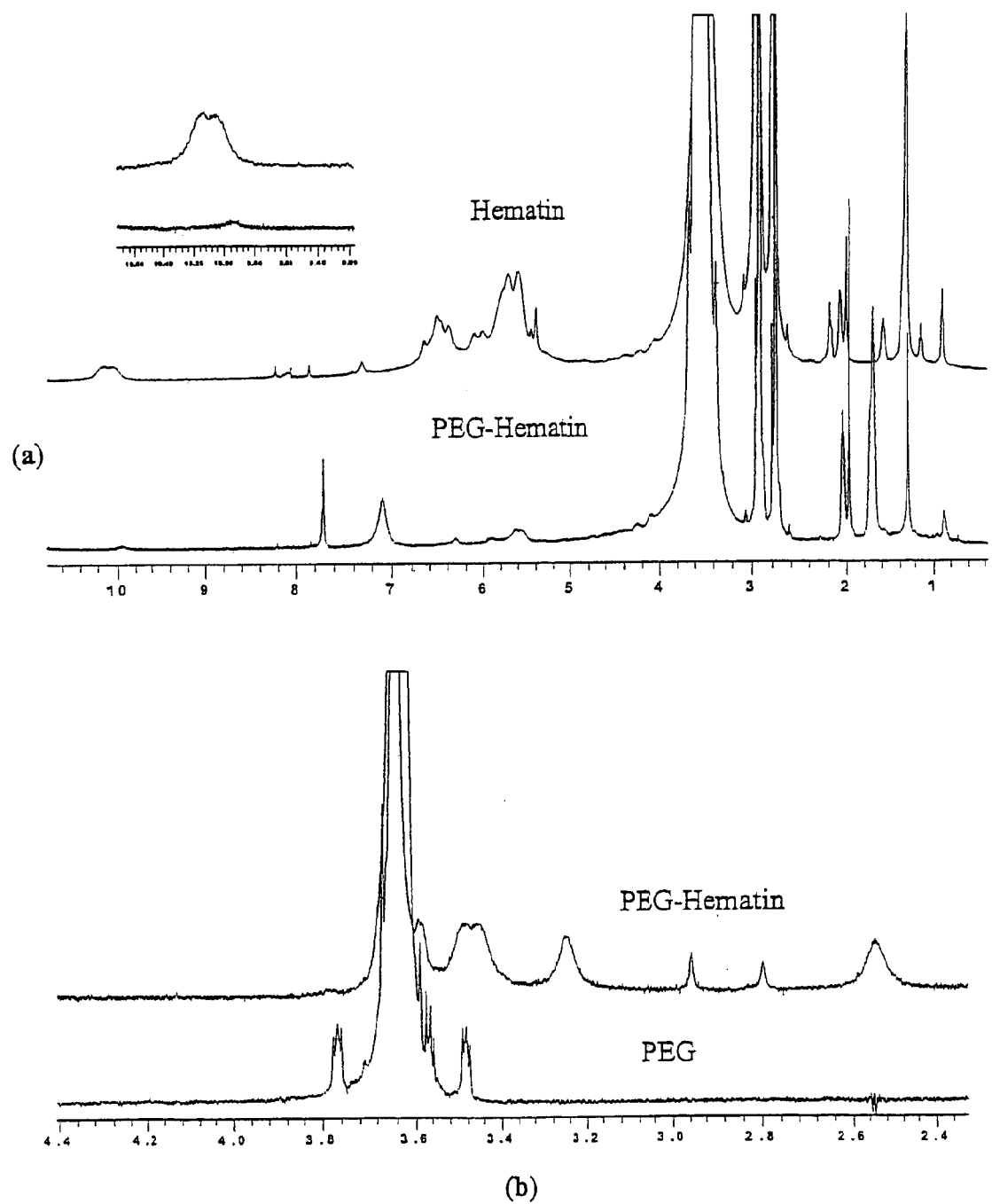
FIG. 3a shows the $^1H$ NMR spectra of hematin and PEG-hematin in DMF-$d_7$. The inset shows the disappearance of the hematin carboxylic acid peak when it is derivatized with PEG.
FIG. 3b shows the $^1H$ NMR spectra of hematin and PEG-hematin in $D_2O$.

An $^1$H NMR spectrum of PEG-hematin in DMF-d$_7$ shows the disappearance of the peak at 10.2 ppm, which was assigned to the carboxylic proton of hematin (FIG. 3a). This clearly indicated that the carboxylic acid hydroxyl moiety was transformed into an ester. The large broad peak at 3.8 ppm was assigned to the poly (ethylene glycol) protons. However the spectra could not be well resolved in the region of 2-4 ppm due to the interference of the peaks assigned to the residual protons in deuterated DMF. In order to get a better resolution of the spectrum, the solvent system was changed to deuterated water. The spectrum in D$_2$O could not be used to distinguish the absence of the carboxylic acid proton due to proton exchange with D$_2$O. However, comparison of the spectrum of PEG-hematin and the spectrum of poly(ethylene glycol), in D$_2$O showed the changes in the position of the PEG peaks of PEG-hematin in comparison to PEG alone. It was found that PEG exhibited a major peak at 3.8 ppm, which was assigned to the bulk of the polymer chains, while the adjoining peaks (triplets) were assigned to the end groups of the polymer. When a PEG-hematin derivative was formed, the peak at 4.0 ppm shifted upfield and merged into the main peak. This was accompanied by considerable broadening and a shift of the peak at 3.8 ppm to 3.6 ppm (FIG. 3b). It was postulated that methylene protons α to the hydroxy group of PEG, on being attached by an ester linkage to hematin, shifted upfield while methylene protons β to the hydroxy groups of PEG were affected by the inhomogeneous paramagnetic environment, leading to broadening. These observed changes strongly indicated the formation of an ester bond between PEG and hematin.

Figure 4:
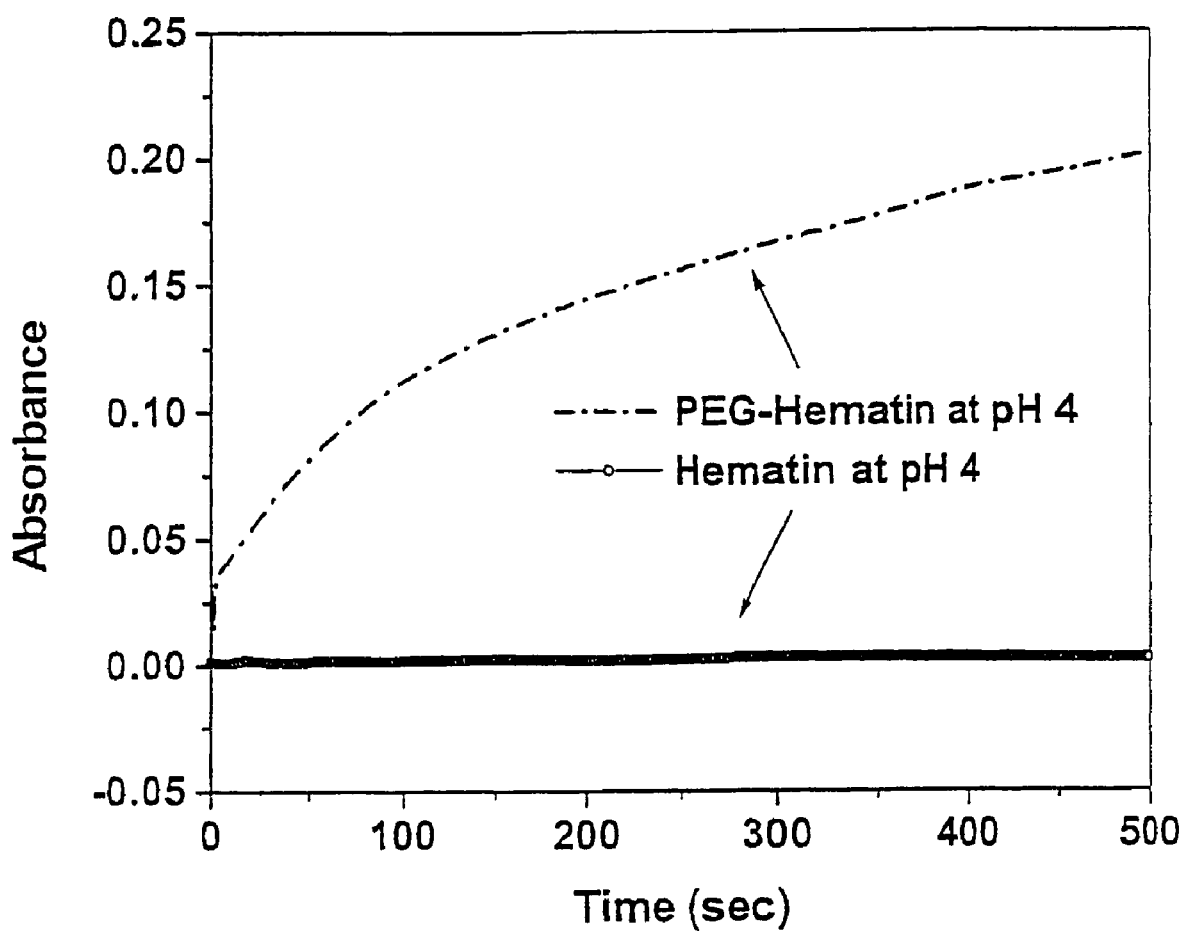
FIG. 4 shows the catalytic activity of hematin and PEG-hematin for the oxidation of pyrogallol at pH 4.0.

The activity of the PEG-hematin was assessed through the oxidation of pyrogallol (0.5%) to purpurogallin in 14 mM potassium phosphate buffer in the presence of 0.027% (w/w) hydrogen peroxide. Interestingly, the activity of the PEG-hematin was found to be approximately 30-fold higher as compared to native hematin at a pH 4.0 (FIG. 4). Without being bound to any particular theory, it is believed that the activity of hematin is dependent on its solubility. Thus, the enhanced activity of the PEG-hematin is attributed to its enhanced solubility.

EXAMPLE 2

Synthesis of Polyaniline

Figure 5:
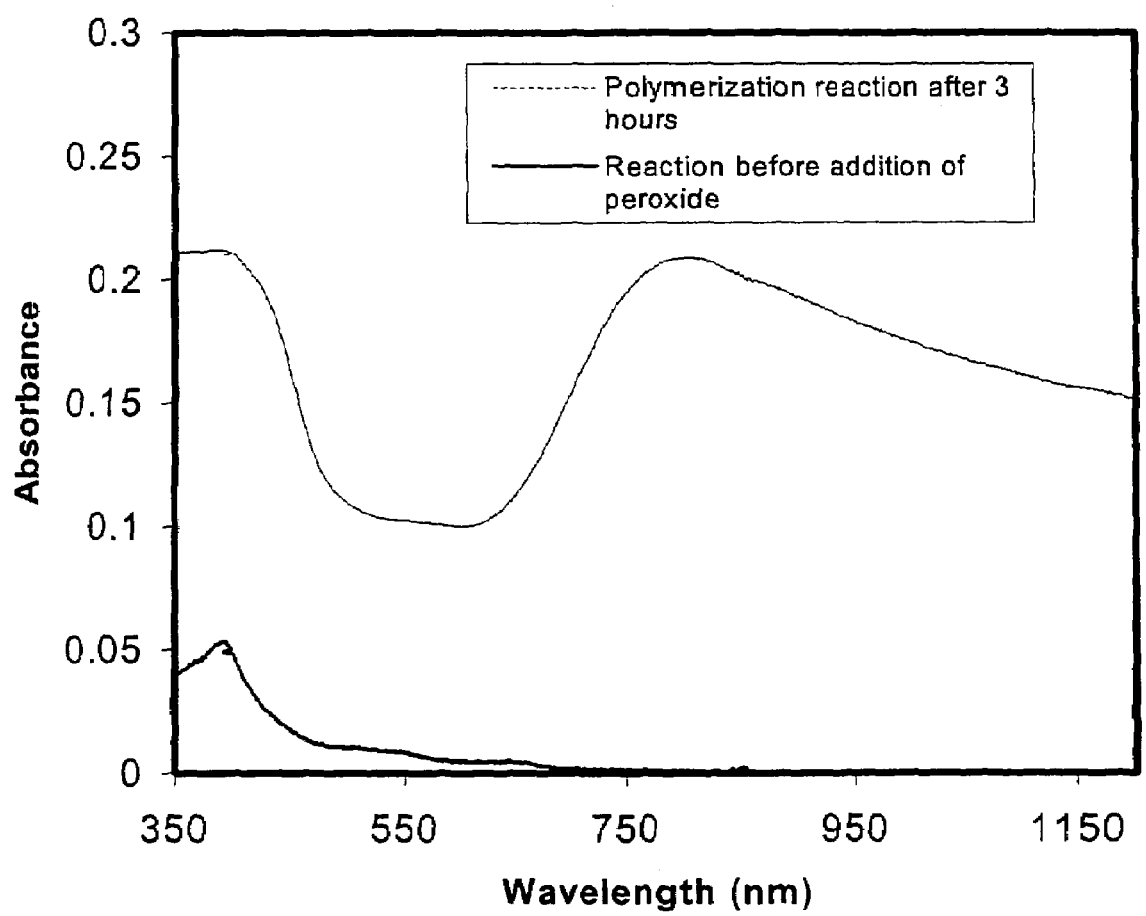
FIG. 5 shows the UV-vis absorption spectrum of aniline monomers and of polyaniline formed during PEG-hematin catalyzed polymerization.

The polymerization of aniline was carried out in 0.1 M sodium phosphate buffer (10 mL) maintained at pH 1. To this buffer solution the aniline monomer was added. The catalyst, PEG-hematin (60 µg), was added only just prior to the addition of hydrogen peroxide. The polymerization was initiated by the incremental addition of a stoichiometric amount of hydrogen peroxide, with respect to aniline. 0.3% H$_2$O$_2$ (w/v) was used with constant stirring and the progress of the reaction was monitored spectroscopically (FIG. 5). Typically, all reaction systems were left stirred until completion of polymerization followed by precipitation of the polyaniline. The Pani synthesized was filtered off and thoroughly washed with acetone few times followed by drying in a vacuum oven. The conductivity of the Pani pellet was found to be of the order of 0.2 S/cm.

This reaction thus proved the versatility and ability of the PEG-Hematin for the synthesis of stable conducting polyaniline even in the absence of template. The polyaniline formed in this case was again redox reversible as proved by cyclic voltammetry studies.

EXAMPLE 3

Synthesis of Sodium Poly(Sodium-4-styrenesulfonate)-Polyaniline Complex

The polymerization of aniline was carried out in 0.1 M sodium phosphate buffer over a range of pH conditions from pH 1-4. A 17 mM solution of sodium polystyrene sulfonate (SPS) template in phosphate buffer (100 mM) was prepared to which the aniline monomer was added in a 1:1 molar ratio of aniline to sodium styrene sulfonate monomer. The catalyst, PEG-hematin (5 mg), was added just prior to the addition of hydrogen peroxide. The polymerization was initiated by the incremental addition of a stoichiometric amount of hydrogen peroxide (relative to aniline). In all cases, 0.3% $H_2O_2$ (w/v) was used with constant stirring, and the progress of the reaction was monitored spectroscopically. On completion of polymerization, the solution was transferred to individual regenerated natural cellulose membrane bags (molecular weight cut-off 10,000 D) and were dialyzed against 5000 mL of acidified deionized water maintained at pH 4.0 to remove unreacted monomers and oligomers. The solid SPS-polyaniline complex was obtained by evaporation of the deionized water followed by drying in a vacuum oven.

Figure 6:
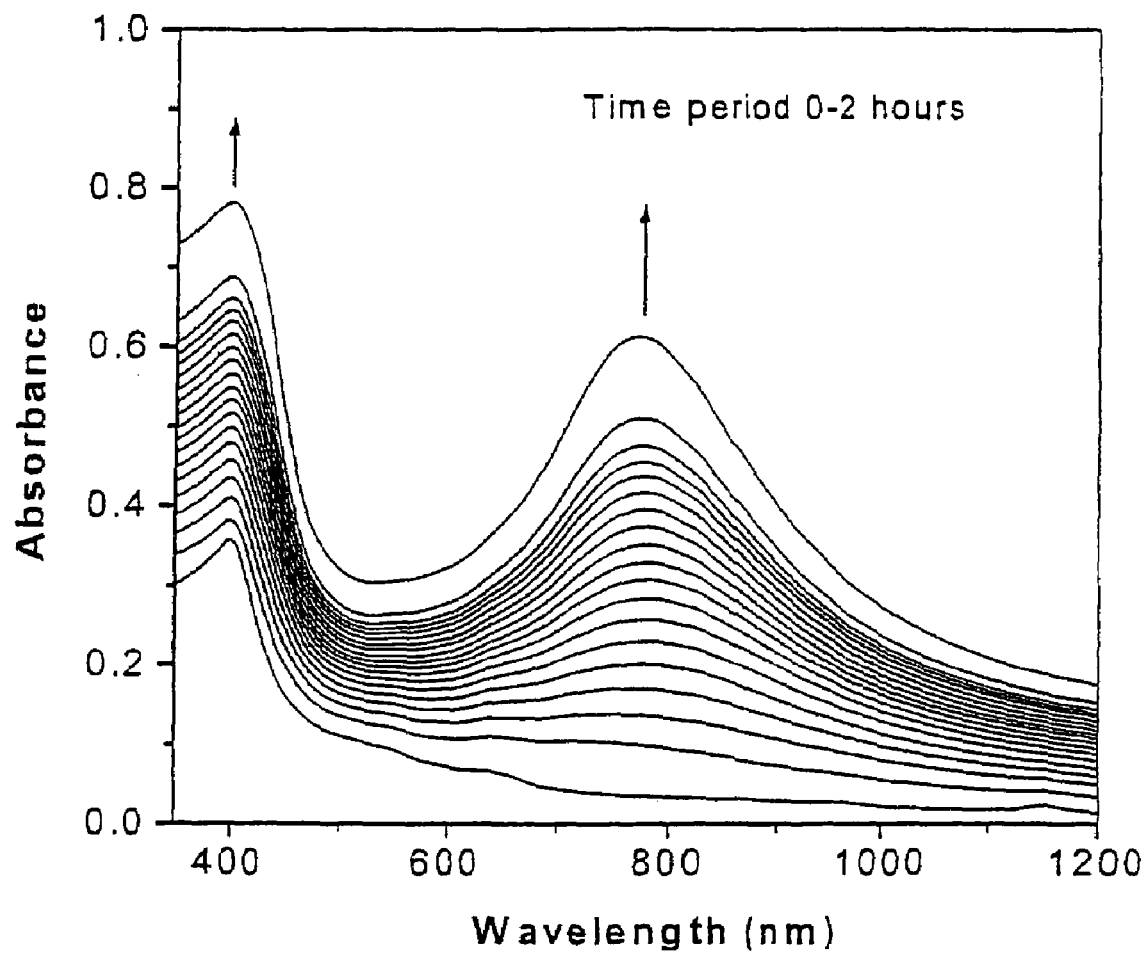
FIG. 6 shows the time dependent UV-vis absorption spectra of the polyaniline-sodium polystyrene sulfonate (SPS) complex formed at pH 4 over 2 hours after initiation of polymerization.
Figure 7:
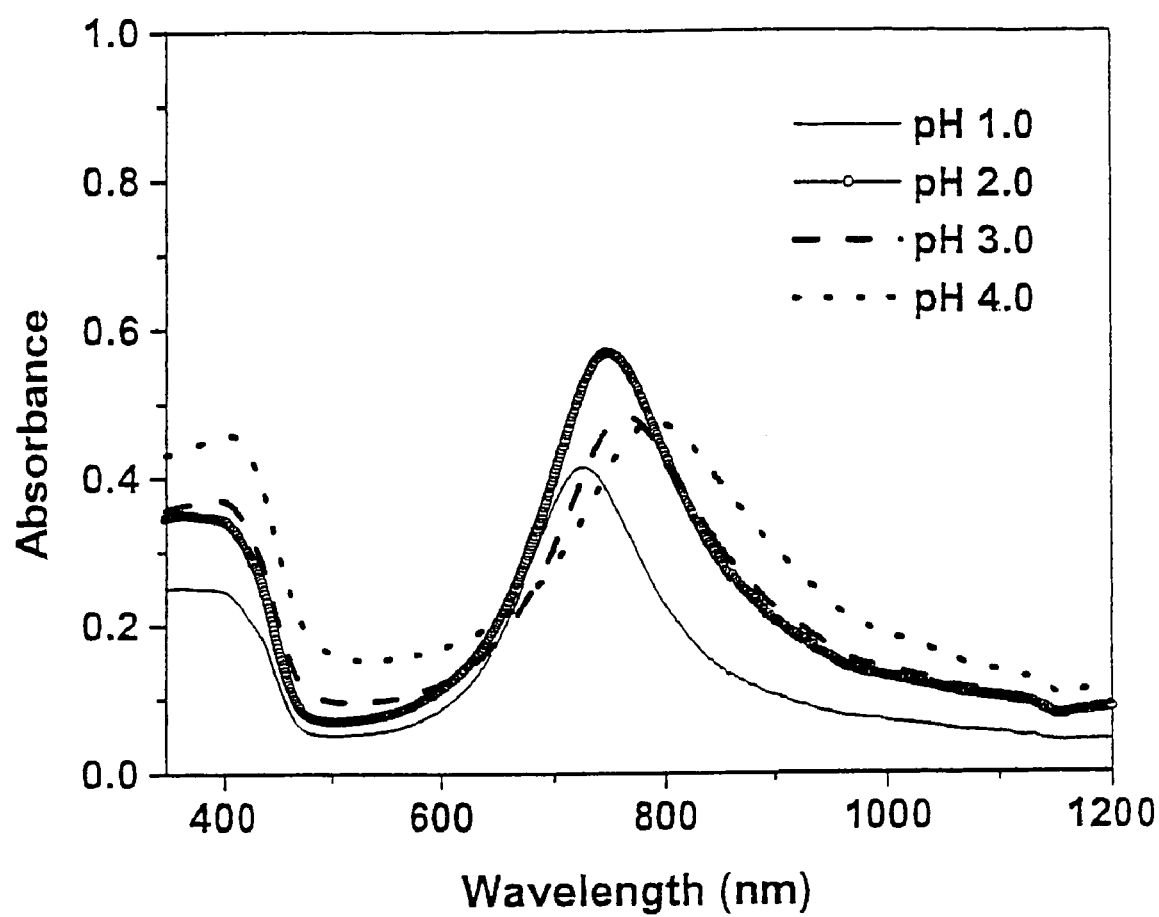
FIG. 7 shows the pH-dependent UV-vis absorption spectra of the polyaniline-SPS complex formed after initiation of polymerization.

It was observed that the solution slowly turned dark green indicating the formation of the doped emeraldine salt form of conducting polyaniline (polyaniline is hereinafter referred to as "Pani"). The UV-vis absorption spectra of the Pani/SPS complex formed at different time intervals over a time period of 2 hours at pH 4.0 after initiation of polymerization reaction is shown in FIG. 6. The UV-vis spectra showed the presence of polaron absorption bands at 400 nm and 800-1200 nm which was consistent with the formation of the conducting form of polyaniline. This polymerization was also carried out at different pH values ranging from pH 1.0 to pH 4.0 as shown in FIG. 7. The formation of polyaniline was observed in all cases, thus demonstrating the stability and robustness of the PEG-hematin in comparison to hematin (insoluble at low pH) or horseradish peroxidase, HRP (denatured at low pH). Also the polyaniline formation reaction catalyzed by PEG-hematin was found to be complete with greater than 90% yield within a few hours, while the unmodified hematin showed little or no reactivity within the same time period under these acidic conditions.

Figure 8:
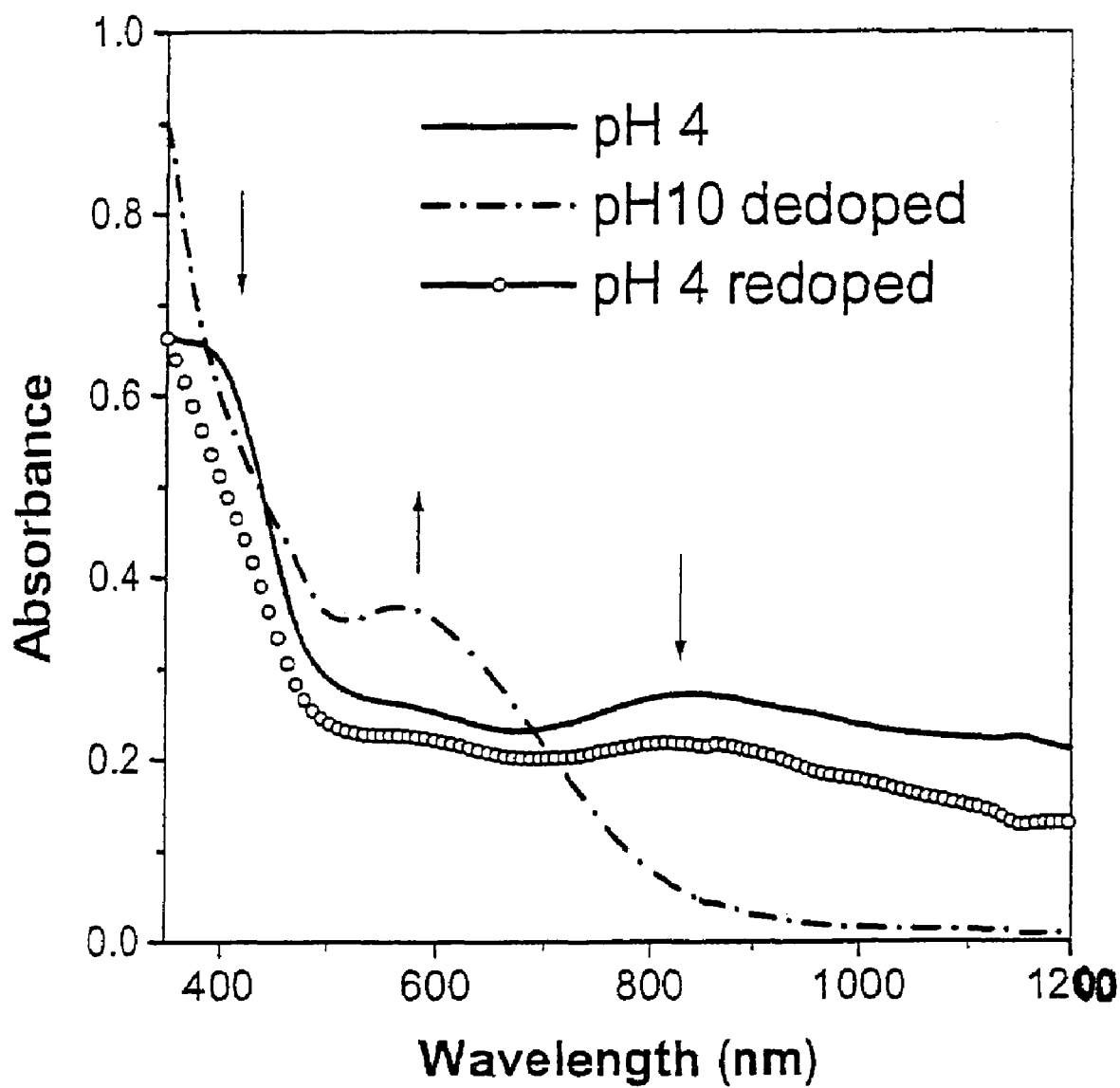
FIG. 8 shows the UV-vis absorption spectra of a polyaniline-SPS complex as it is titrated with 1 N NaOH and 1 N HCl, demonstrating that the complex can be reversibly dedoped and redoped using base or acid, respectively.

The redox tunability of the polyaniline formed was further demonstrated by dedoping the emeraldine salt form of Pani at high pH and then redoping with acid. With increasing pH (dedoping) on titration with 1 N NaOH, the polaron bands at 400 nm and 800 nm were found to diminish, while a new band at 600 nm began to emerge due to the exciton transition of the quinoid ring giving rise to a blue solution indicating that the Pani has been fully dedoped to the base form. On titrating the solution back with 1 N HCl (redoping), a reversible color change was observed and the spectra is shown in FIG. 8. Furthermore, an isosbestic point at 710 nm was also observed, which was indicative of the changes in the polyaniline oxidation state. This behavior was similar to the polyaniline synthesized chemically or enzymatically with HRP and confirmed the formation of the conducting polyaniline emeraldine salt form (electroactive form) catalyzed by PEG-hematin.

The conductivity of the emeraldine salt form of polyaniline synthesized at pH less than 4 was found to be about $10^{-3}$ S/cm.

Figure 9:
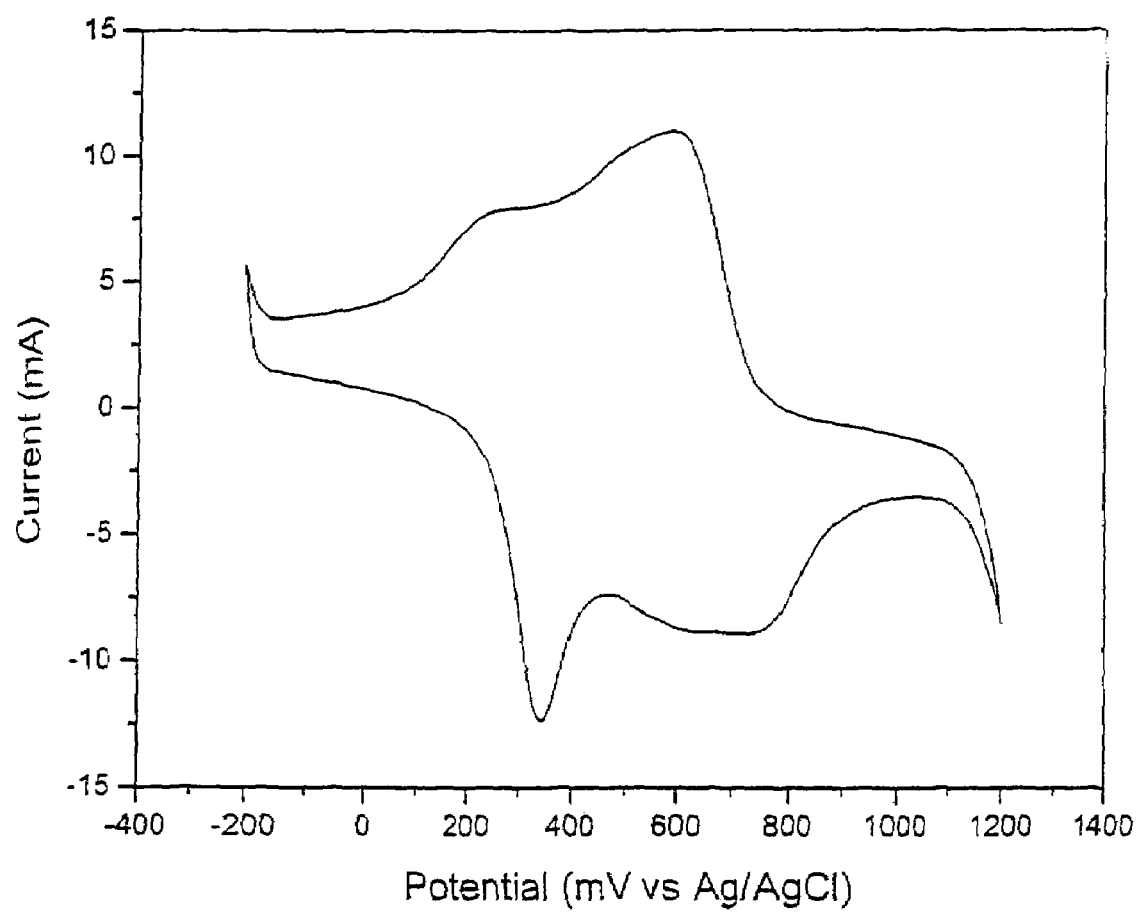
FIG. 9 shows a cyclic voltammogram of a solution cast film of polyaniline-SPS complex synthesized at pH 1.0.

Furthermore, cyclic voltammetry studies were carried out to determine the electrochemical nature of polyaniline synthesized by the PEG-hematin catalysis. The cyclic voltammogram of a cast film of an SPS-Pani complex (FIG. 9) showed two sets of peaks indicating two reversible redox cycles at a scan rate of 100 mV/s over a potential window of −0.2-1.2 V.

EXAMPLE 4

Figure 10:
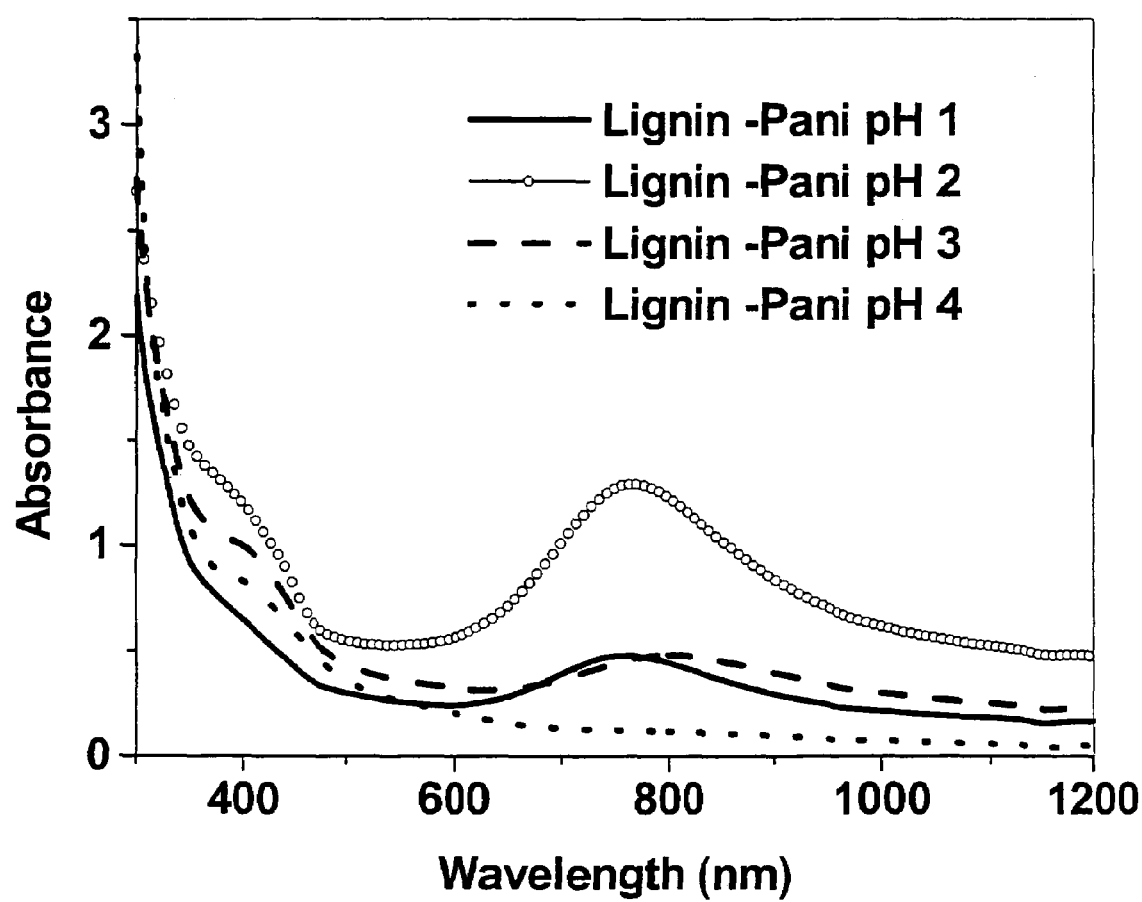
FIG. 10 shows the pH-dependent UV-vis absorption spectra of polyaniline-lignin sulfonate complexes formed during polymerization.

Synthesis of Lignosulfonate-Pani Complex 5.2 mg of a lignin sulfonate polyelectrolyte complex was dissolved in 10 mL of sodium monophosphate buffer (0.1 M) maintained at pH 4.0. This was followed by the addition of 18 µL of aniline, a catalytic amount of PEG-Hematin and a amount of hydrogen peroxide (0.3%) stoichiometric with aniline. The reaction mixture was allowed to stir until precipitation of the polyelectrolyte-Pani complex ceased. The reaction was also carried out in solutions having pHs ranging from pH 1-4 (FIG. 10). The precipitated lignin sulfonate-Pani complex obtained was washed several times with acidified acetone to remove the unreacted monomer and finally washed with acidified deionized water, filtered under suction through a polycarbonate filter and dried in a vacuum oven to yield lignin sulfonate-polyaniline complex.

When the polymerization was conducted at pH 3.0, there was a peak of low intensity at 767 nm for the emeraldine form of polyaniline, which was completely absent during polymerization at pH 4.0. The extended absorption until 1200 nm indicated the formation of the extended conjugation of the polyaniline backbone. Thus the synthesis of Pani complexed with a natural polymer further widens the scope of applications to other natural polyelectrolytes to form versatile, environmentally benign conducting polymers.

EXAMPLE 5

Synthesis of DNA-Pani Complex

The polymerization of aniline in the presence of Calf Thymus DNA was carried out in sterile 10 mM phosphate buffer. A 1.0 mM calf thymus DNA solution was prepared by dissolving the required amount of DNA in 10 mL of sterilized sodium phosphate buffer maintained at pH 4. The concentration of DNA was determined by the UV absorbance at 258 nm. To this DNA solution, 4.5 µl (5 mM) of aniline was added. The pH of the solution was again checked and adjusted to 4.3, and 5 mg of PEG-Hematin were added. To this reaction mixture, a solution of hydrogen peroxide (0.3% solution, 4.5 µl, 5 mM) was added drop-wise, to initiate the polymerization and the reaction of aniline was followed using UV-Vis spectroscopy and circular dichroism polarimetry.

Figure 11:
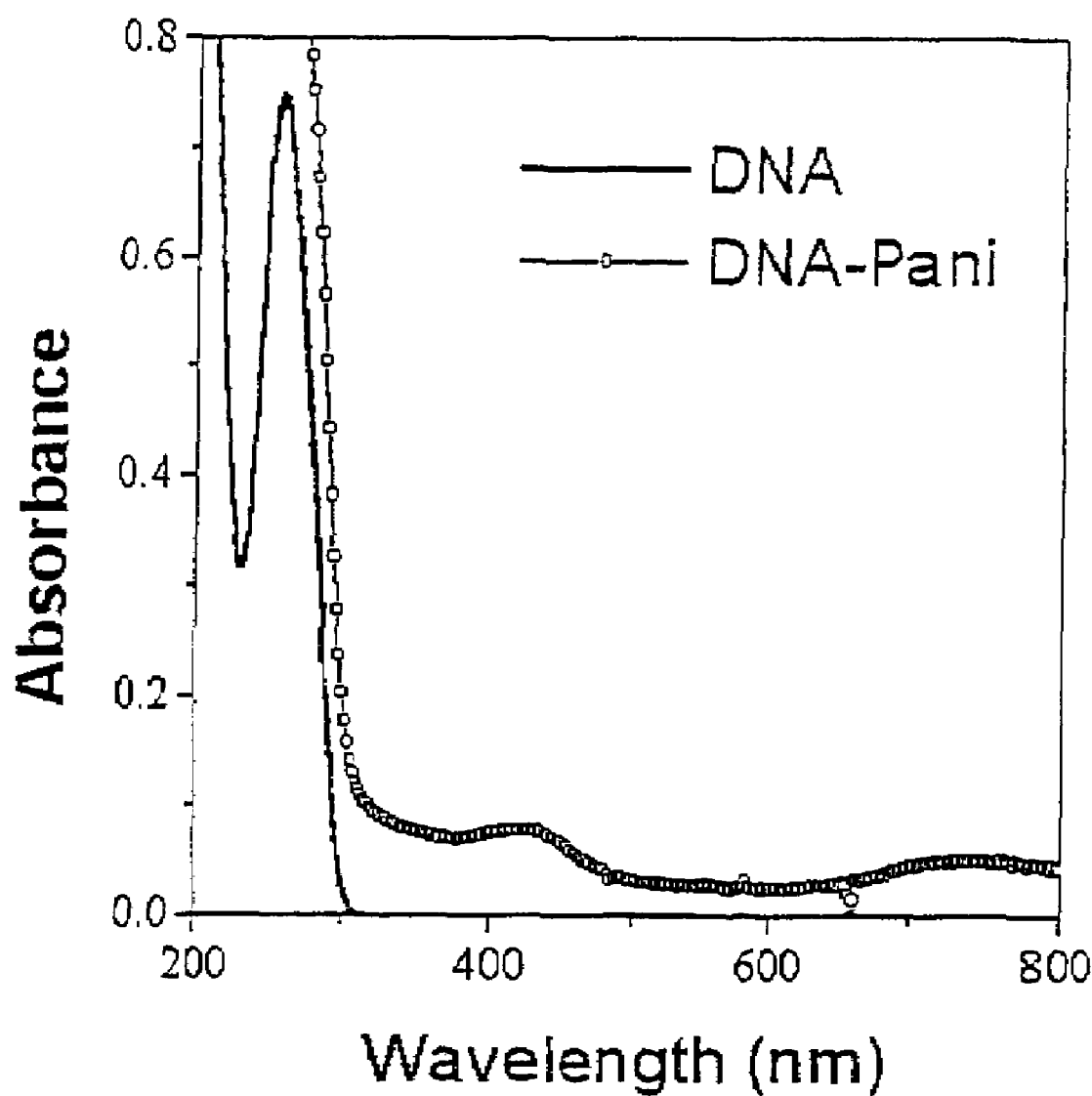
FIG. 11 shows UV-vis absorption spectra of polyaniline-DNA formed during PEG-hematin catalyzed polymerization.

When the aniline monomer was added to a DNA solution at pH 4.3, the electrostatic interaction between the protonated aniline monomers and the phosphate groups in the DNA caused the monomers to closely associate with the DNA. The association of the protonated aniline monomer on the DNA template facilitated a predominantly para-directed coupling and inhibited parasitic branching during the polymerization. The high proton concentration around the phosphate groups also provided a unique local lower pH environment that permitted the polymerization of aniline at a higher pH than that necessary with conventional chemical polymerization of aniline. The polymerization was catalyzed by PEG-hematin and initiated by hydrogen peroxide. However, as the polymerization proceeded over a period of time and a critical chain length was attained, the DNA-Pani complex precipitated out of solution. It was concluded that the complex remained soluble as long as there were enough phosphate groups on the DNA available for solvation. As the polymerization proceeded, the preferred molecular interaction between the charged aniline groups and the phosphate groups of DNA caused the growing chain to occupy a majority of these sites leading to the salting out of the DNA-Pani complex. The polymerization reaction was followed using UV-vis spectroscopy and circular dichroism polarimetry. The UV-vis spectra of the DNA-Pani complex recorded after initiation of the polymerization are shown in FIG. 11. The UV-vis absorbance spectra showed a peak around 260 nm emerging from the absorption of the base pairs of DNA along with polaron absorption bands at 420 nm and 750 nm, indicating the formation of the conducting emeraldine salt form of polyaniline.

Figure 12:
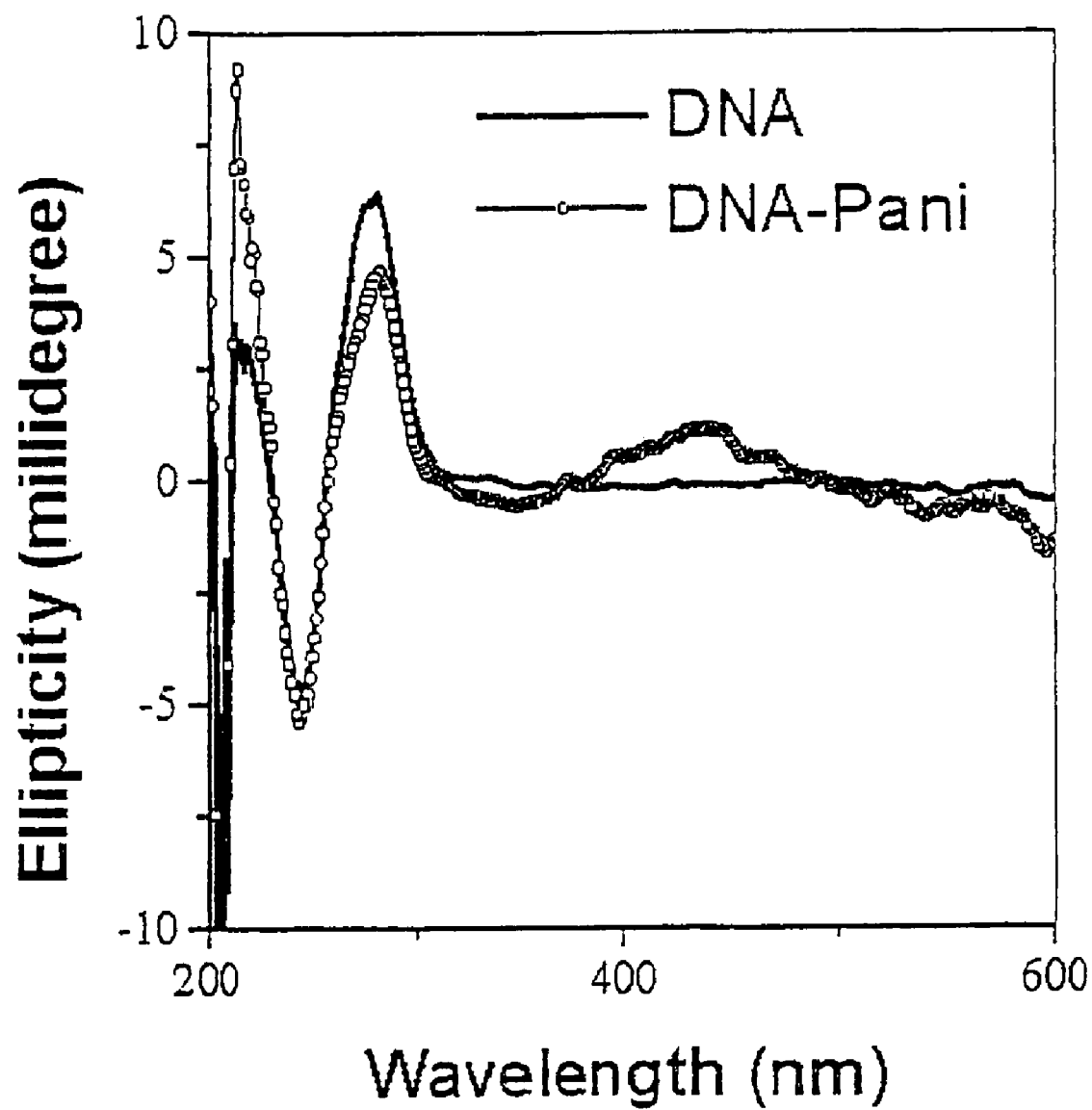
FIG. 12 shows CD spectra of polyaniline-DNA formed during PEG-hematin catalyzed polymerization.
Figure 13:
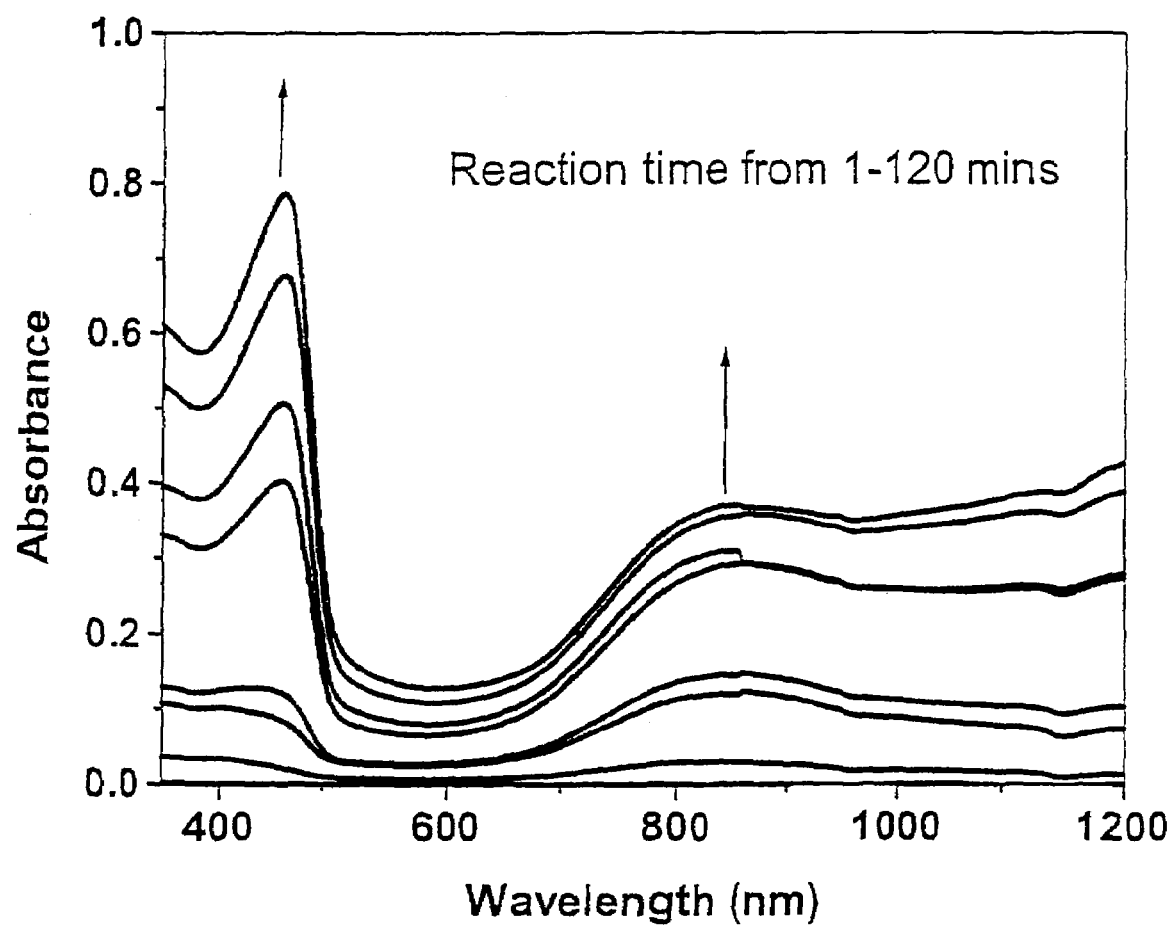
FIG. 13 shows time-dependent UV-vis absorption spectra of the polymerization of 2-methoxy-5-methylaniline catalyzed by PEG-hematin.

The bases in the nucleic acid have a plane of symmetry and thus are not intrinsically optically active. However, the deoxyribose sugar is asymmetric and since the bases are attached to the anomeric carbon of these sugars, the sugar can induce a circular dichroism in the absorption bands of the bases. These bands may be observed either for the intensely electronically allowed π-π* transitions, or for the weakly allowed n-π* transitions because these transitions are magnetically allowed. Also the π electron systems of the bases make them hydrophobic, so the bases tend to stack in hydrogen-bonding solvents to minimize the π-electron surface area exposed to the solvent. The hydrophobic planes and hydrophilic edges as well as charge-charge interactions cause the bases to stack and the polymer to adopt a helical structure. Preferential handedness is induced in these helical structures by the intrinsically asymmetric sugars, giving the DNA polymer a whole super asymmetry. The electronic transitions of these chromophoric bases are in close proximity and can thus interact to give well-defined CD spectra. The CD spectrum of the DNA-Pani complex showed a reduction in the intensity of the peak at 275 nm (FIG. 12). This change indicated a polymorphic transition in DNA causing the DNA to change from a loosely wound form to the over-wound form. The appearance of a positive peak at 450 nm indicated that the helical polyelectrolyte DNA template induces a macroscopic order in the Pani that is formed. This result proves the extensive versatility of the PEG-Hematin catalyst with a variety of templates including delicate biomacromolecules in providing the optimal catalytic activity for polymerization.

EXAMPLE 6

Synthesis of Poly(2-methoxy-5-methylaniline)-SPS Complex

The polymerization of 2-methoxy-5-methylaniline (2M5M) was carried out in 0.1 M sodium phosphate buffer of pH 4.0. A 17 mM SPS template solution, as measured from the concentration of sodium styrene sulfonate monomers, in phosphate buffer (10 mL) was prepared to which 2M5M (24 mg) was added in the desired (1:1, 2M5M:SPS) molar ratio. The polymerization was initiated after addition of 5 mg of PEG-Hematin, by the incremental addition of an amount of peroxide (0.3% w/v) stoichiometric with 2M5M, with constant stirring. The progress of the reaction was monitored spectroscopically. After the reaction was complete, the solution was dialyzed to remove the unreacted monomers, followed by evaporation to yield a SPS-poly (2M5M) complex.

Figure 14:
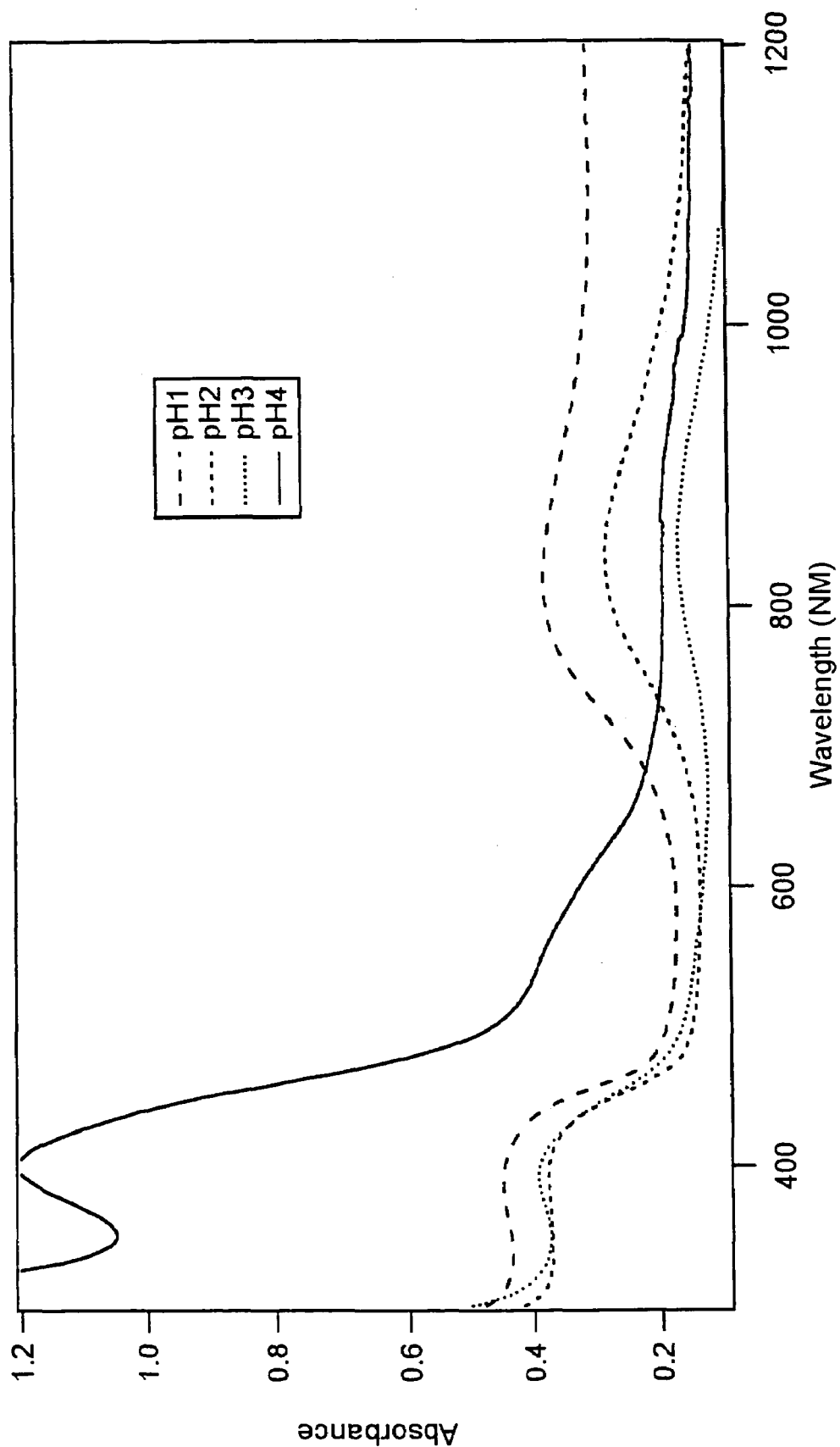
FIG. 14 shows pH-dependent UV-vis absorption spectra of polyaniline-dodecylbenzenesulfonic acid complexes formed during polymerization.

The UV-vis absorption spectra of the poly (2M5M)/SPS complex formed is shown in FIG. 14. The spectra again showed the presence of a polaron band at 425 nm and extended conjugation in the longer wavelength range indicating the linear conducting form of polyaniline. This polymer also showed reversible redox tunability similar to that observed for the SPS-polyaniline complex formed in Example 2. The SPS-poly(2M5M) formed could also be reversibly de-doped on titrating with 1 N NaOH and re-doped by back titrating with 1N HCl.

EXAMPLE 7

Synthesis of Sodium Dodecylbenzenesulfonic Acid-Pani Complex

Polymerization of aniline was carried out in 0.1 M sodium phosphate buffer at pH 4. A 17 mM solution of dodecylbenzenesulfonic acid (DBSA) in phosphate buffer (100 mM) was prepared to which the aniline monomer was added in the desired (1:1, Aniline:DBSA) molar ratio. The catalyst, PEG-Hematin (5 mg), was added just prior to the addition of hydrogen peroxide. The polymerization was initiated by the incremental addition of an amount of hydrogen peroxide stoichiometric to aniline. In all cases, 0.3% $H_2O_2$ (w/v) was used with constant stirring. The progress of the reaction was monitored spectroscopically.

EXAMPLE 8

Synthesis of SPS-Polyphenol Complex

A polymerization reaction was carried out in 10 mL of aqueous phosphate buffer (100 mM). The pH of the reaction media for the phenol polymerization was maintained at pH 7.0 and equimolar concentrations (17 mM) of SPS, with respect to the concentration of the repeat units, and phenol monomer were added to the buffered solution, followed by 10 mg of the PEG-hematin. The reaction was initiated by addition of a stoichiometric, with respect to phenol, amount of $H_2O_2$ (30% w/v) in one lot to facilitate the formation of high molecular weight polyphenol. The reaction was monitored spectroscopically. A control experiment was also carried out simultaneously in the absence of catalyst. The final products were dialyzed using Centricon concentrators (10,000 Mw cut off, Amicon Inc., Beverly, Mass.) to remove unreacted monomers. The samples were then dried under vacuum at 50° C. and used for further analysis. The yield was calculated to be typically 95% or higher.

Figure 15:
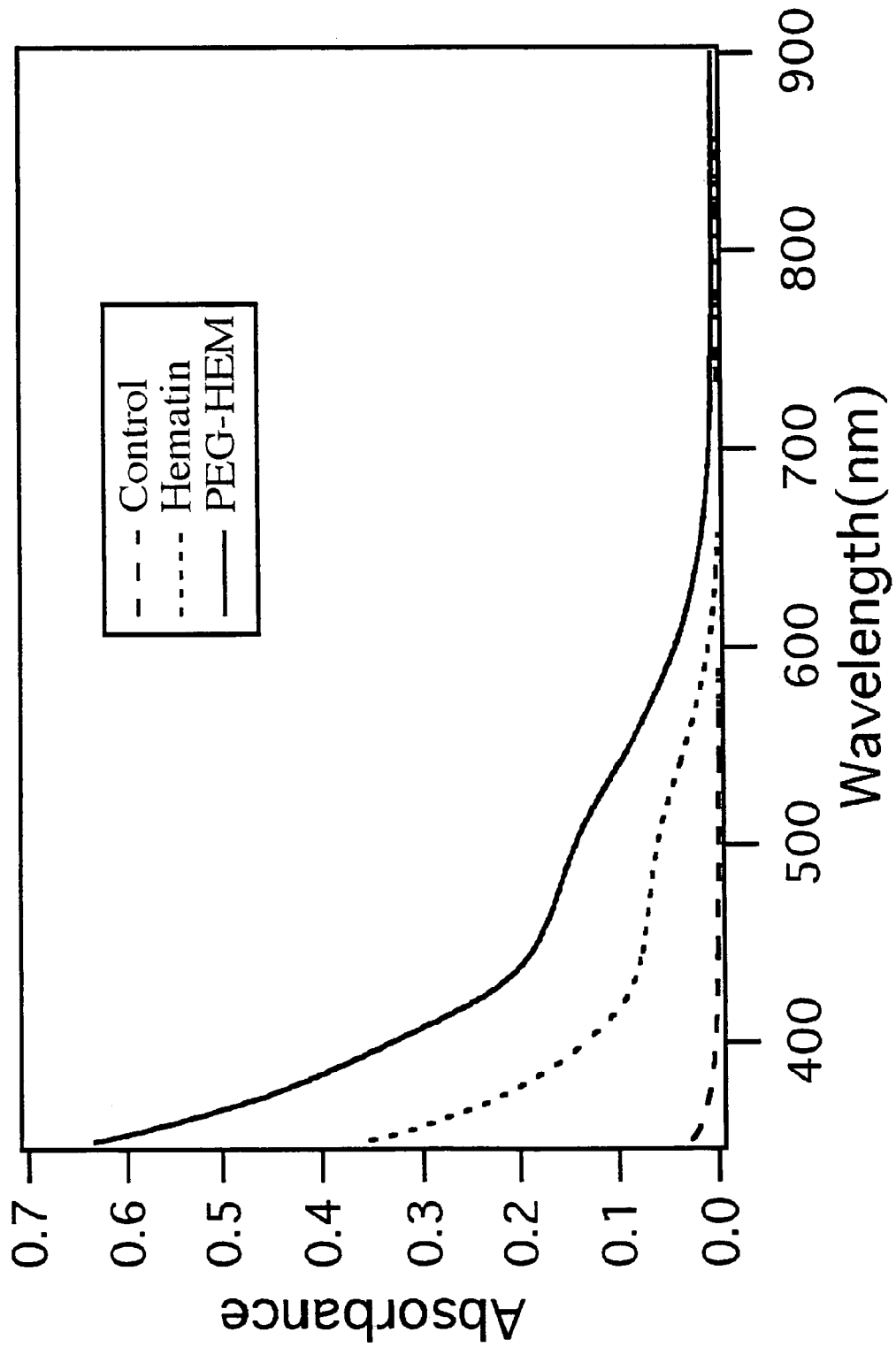
FIG. 15 shows UV-vis absorption spectra of a SPS-polyphenol complex formed during polymerization.

The PEG-hematin complex was also found to catalyze the polymerization of phenol at pH 7.0 more efficiently than that compared to the native hematin and peroxidase (FIG. 15). The large broad absorption tail in the region from 300-700 nm confirmed the presence of extended conjugation and indicated formation of polyphenol by PEG-hematin reaction. In comparison, the absorption of the hematin-catalyzed reaction is relatively weak. Thus, modification of the hematin with PEG was observed to significantly improve the reactivity to suit the desired reaction conditions leading to the formation of polyphenol.

EXAMPLE 9

Preparation of Assembled Hematin

Glass slides (25 by 75 mm) were hydrophilized with 1% Chem-solv solution in deionized water under ultrasonication for use as substrates. This treatment generates negative charges on the surface of the slides due to partial hydrolysis. After 3 hr, the slides were ultrasonicated twice in deionized water for 30 min before use.

The electrostatic layer-by-layer deposition process was carried out in two steps. Poly(diallyldimethylammonium chloride) (PDAC) (10 mM) and hematin (3 mM) solutions were prepared over a pH range from 5 to 11. In the first step, hydrophilized glass slides were immersed in PDAC solution for 10 min at room temperature and washed with deionized water for 5 min. After the deposition and washing steps, the slides were dried with a stream of nitrogen. In the second step, the substrates with a single layer of PDAC were immersed into the hematin solution for 10 min and subsequently washed with deionized water and dried with a stream of nitrogen to produce an assembled hematin, having a bilayer film of PDAC/hematin. This dipping procedure was iterated to build up multilayer films.

EXAMPLE 10

Synthesis of Pani-SPS Complex Using Assembled Hematin

Polymerization of aniline was carried out at room temperature in a 40 mL, 0.1M phosphoric acid buffer solution, which contained a 1:1 molar ratio of SPS (MW 1,000,000; moles correspond to quantity of monomers units) to aniline 0.167 g (0.81 mmol). SPS was added first to the buffered solution, followed by an addition of 2.1 mL of aniline stock solution (0.036 mL aniline to 1 mL buffer at pH 1.4) with constant stirring. A seventeen bilayer Hematin/PDAC assembly was immersed in the solution. To initiate aniline polymerization, 11 mL of 0.25% $H_2O_2$ was added dropwise, incrementally, over 30 min. The reaction was maintained for 24 h, and carried out at different pH values (1.0, 2.0, 3.0). The rate of assembled hematin catalyzed polymerization was monitored by a Perkin-Elmer Lamda-9-UV-vis spectrophotometer at room temperature.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of polymerizing an aromatic monomer, comprising combining an aromatic monomer with a hematin catalyst in a buffered solution having a pH in a range of between about pH 0 and about pH 4, wherein the hematin catalyst has been derivatized with one or more non-proteinaceous amphipathic groups, and wherein the derivatized hematin catalyst is dissolved in the solution.

2. The method of claim 1, further comprising combining a peroxide initiator with the aromatic monomer and the derivatized hematin.

3. The method of claim 2, further comprising a template, wherein the aromatic monomer aligns along said template and polymerizes to form a complex comprising the polymerized aromatic monomer and the template.

4. The method of claim 3, wherein the template is a polyelectrolyte.

5. The method of claim 4, wherein the polyelectrolyte is polyanionic.

6. The method of claim 5, wherein the polyanionic polyelectrolyte is poly(styrene sulfonic acid) or a salt thereof.

7. The method of claim 3, wherein the template is optically active.

8. The method of claim 7, wherein the optically active template is an oligonucleotide or a polynucleic acid or a salt thereof.

9. The method of claim 8, wherein the polynucleic acid is 2'-deoxyribonucleic acid or a salt thereof.

10. The method of claim 5, wherein the template is lignin sulfonic acid or a salt thereof.

11. The method of claim 5, wherein the template is dodecylbenzene sulfonic acid or a salt thereof.

12. The method of claim 3, wherein the aromatic monomer is a substituted or unsubstituted aromatic compound.

13. The method of claim 12, wherein the aromatic compound is an aniline.

14. The method of claim 13, wherein the aniline is 2-methoxy-5-methylaniline.

15. The method of claim 12, wherein the aromatic compound is a phenol.

16. The method of claim 13, wherein the complex formed is a water-soluble complex of a polyaniline and the template.

17. The method of claim 16, wherein the polyaniline is of the electrically-conducting emeraldine salt form.

18. The method of claim 15, wherein the complex formed is a water-soluble complex of polyphenol and the template.

19. The method of claim 7, wherein the polymerized aromatic monomer complexed to the template has a macroasymmetry.

20. The method of claim 1, wherein the non-proteinaceous amphipathic groups are selected from the group consisting of phosphoglycerides; sphingomyelin; glycolipids; substituted or unsubstituted polyethers; substituted or unsubstituted polyalkylene glycols; substituted or unsubstituted polyamines; polyammonium groups; and polysaccharides.

21. The method of claim 20, wherein the polyamines are selected from the group consisting of polyethyleneimine, polyallylamine and poly(diallylamine).

22. The method of claim 20, wherein the polyammonium group is selected from the group consisting of poly(allylammonium salts), poly(trimethylallylammonium salts), poly(triethylallylammonium salts), poly(dimethyldiallylammonium salts) and poly(diethyldiallylammonium salts.

23. The method of claim 20, wherein the polysaccharides are selected from the group consisting of hydroxypropyl cellulose, hydroxymethyl cellulose and hydroxyethyl cellulose.

* * * * *